US006852841B1

United States Patent
Jarman et al.

(10) Patent No.: US 6,852,841 B1
(45) Date of Patent: Feb. 8, 2005

(54) FROZEN FOOD PRODUCT

(75) Inventors: Carl Dudley Jarman, Bedford (GB);
Christopher Michael Sidebottom,
Bedford (GB); Sarah Twigg, Bedford
(GB); Dawn Worrall, York (GB)

(73) Assignee: **Good Humor-Breyers Ice Cream,
division of Conopco, Inc.**, Green Bay,
WI (US)

( * ) Notice: Subject to any disclaimer, the term of this patent is extended or adjusted under 35 U.S.C. 154(b) by 0 days.

(21) Appl. No.: 09/600,787
(22) PCT Filed: Dec. 23, 1998
(86) PCT No.: PCT/EP98/08553

§ 371 (c)(1),
(2), (4) Date: Nov. 24, 2000

(87) PCT Pub. No.: WO99/37782

PCT Pub. Date: Jul. 29, 1999

(30) Foreign Application Priority Data

Jan. 22, 1998 (GB) ............................................. 9801408

(51) Int. Cl.$^7$ ........................ A61K 35/78; A61K 31/01; C07K 14/415
(52) U.S. Cl. ....................... 530/370; 530/300; 530/395; 514/8; 424/93.7; 424/94.61
(58) Field of Search ................................ 530/300, 370, 530/402, 395; 424/94.61, 93.7; 514/8

(56) References Cited

U.S. PATENT DOCUMENTS

| 5,118,792 | A | * | 6/1992 | Warren et al. ............... 530/350 |
| 5,731,419 | A | | 3/1998 | Sarhan et al. |
| 6,090,917 | A | | 7/2000 | Lillford et al. |
| 6,096,867 | A | | 8/2000 | Byass et al. |
| 6,156,880 | A | | 12/2000 | Lillford et al. |
| 6,162,789 | A | | 12/2000 | Lillford et al. |
| 6,348,569 | B1 | * | 2/2002 | Walker et al. ............... 530/300 |

FOREIGN PATENT DOCUMENTS

| CA | 2104142 | 2/1995 |
| GB | 2 315 753 | 2/1996 |
| GB | 2 315 752 | 2/1998 |
| WO | WO 90/13571 | 11/1990 |
| WO | 92/22581 | 12/1992 |
| WO | WO 92/22581 | 12/1992 |
| WO | WO 94/03617 | 2/1994 |
| WO | WO 94/17186 | 8/1994 |
| WO | WO 95/15377 | 6/1995 |
| WO | WO 96/11586 | 4/1996 |
| WO | WO 98/04148 | 2/1998 |
| WO | WO 98/04699 | 2/1998 |

OTHER PUBLICATIONS

Lee, S. P. et al. (1993) Molecular cloning of abscisic acid–responsive mRNAs expressed during the induction of freezing tolerance in bromegrass (*Bromus inermis*Leyss) suspension culture. Plant Physiol. vol. 101,pp. 1089–1096.*
Tase, K. et al. (1996) Analysis of hardening relaed proteins in *Lolium temulentum* L. Grassland Science, vol. 42, pp. 117–122.*
Harison, J. etal. (1997) *Acta physiolodiae* plantarum, vol. 19, pp. 505–515.*
Lee, M. et al. (1990) The reduction of the freezing point of tobacco plants transformed with the gene encoding for the antifreeze protein from winter flounder, J.Cell.Biochem., Suppl. 14E, 303.*
International Search Report (PCT/EP 98/08553).
*Journal Of Plant Physiology*, "Cryoprotective Leaf Proteins: Assay Methods And Heat Stability", Dirk K. Hincha and Jürgen M. Schmitt. 1992. vol. 140, pp. 236–240.
*Plant Molecular Biology*, "Characterization Of A Spinach Gene Responsive To Low Temperature And Water Stress", Lisa G. Neven, Dale W. Haskell, Andres Hofig, Qin–Bao Li, Charles L. Guy, 1993, vol. 21, pp. 291–305.
Abstracts And Reviews, "Abstracts of the Papers Presented at the 18$^{th}$ Annual Meeting of the ASEV/Eastern Section", R. Salzman, vol. 44, No. 4, 1993.
*Biochemical And Biophysical Research Communications*, "A Cold–Regulated Arabidopsis Gene Encodes A polypeptide Having Potent Cryoprotective Activity", C. Lin and M. Thomashow, vol. 183, No. 3, 1992, pp. 1103–1108.
*Plant Physiology*, "DNA Sequence Analysis Of A Complementary DNA For Cold–Regulated Arabidopsis Gene cor15 And Characterization Of The COR 15 Polypeptide", C. Lin and M. Thomashow, (1992), 99, pp. 519–525.
*The Plant Journal*, "Immunolocalization Of Freezing–Tolerance–Associated Proteins In the Cytoplasm And Nucleoplasm Of Wheat Crown Tissues", M. Houde, (1995), 8(4), 583–593.
GB Search Report for Application No. GB 9801408.7 dated Jul. 21, 1998.
*Plant Physiology*, 1994, 104, pp. 971–980—Wai–Ching Hon et al. "Extraction and Isolation of Antifreeze Proteins from Winter Rye (*Secale cereale* L) Leaves".
*Plant Physiology*, 1992, 100, pp. 593–596—Marilyn Griffith et al., "Antifreeze Protein Produced Endogenously in Winter Rye Leaves".

* cited by examiner

Primary Examiner—Karen Cochrane Carlson
Assistant Examiner—Samuel W. Liu
(74) Attorney, Agent, or Firm—Gerard J. McGowan, Jr.

(57) ABSTRACT

Anti-freeze protein comprising at least 40% of the amino acids serine, threonine and asparigine and having at least 80% of sequence identity with the amino acid sequence of SEQ ID NO:1 as well as modified forms thereof.

10 Claims, No Drawings

FROZEN FOOD PRODUCT

TECHNICAL FIELD OF THE INVENTION

The invention relates to anti-freeze proteins (AFPs) and frozen food product containing AFPs.

BACKGROUND TO THE INVENTION

Anti-freeze proteins (AFPs) have been suggested for improving the freezing tolerance of foodstuffs. For the purpose of the invention, the term AFP has the meaning as well-known in the art, namely those proteins which exhibit the activity of inhibit the growth of ice crystals. See for example U.S. Pat. No. 5,118,792.

WO 90/13571 discloses antifreeze peptides produced chemically or-by recombinant DNA techniques. The AFPs can suitably be used in food-products. Example 3B shows modified ice crystal shapes if a water-ice mixture is frozen into a film in combination with 0.01 wt % of AFP.

WO 92/22581 discloses AFPs from plants which can be used for controlling ice crystal shape in ice-cream. This document also describes a process for extracting a polypeptide composition from extracellular spaces of plants by infiltrating leaves with an extraction medium without rupturing the plants.

WO 94/03617 discloses the production of AFPs from yeast and their possible use in ice-cream. WO 96/11586 describes fish AFPs produced by microbes.

Several literature places also mention the isolation and/or use of plant proteins for cryoprotection. Cryoprotective proteins have a function in the protection of plant membranes against frost damage. These proteins, however, do not possess recrystallisation inhibition properties and are, therefore, not embraced within the terms AFPs.

Hincha in Journal of Plant Physiology, 1992, 140, 236–240 describes the isolation of cryoprotective proteins from cabbage. Volger in Biochimica et Biophysica Acta, 412 (1975), 335–349 describes the isolation of cryoprotective leaf proteins from spinach. Boothe in Plant Physiol (1995), 108: 759–803 describes the isolation of proteins from *Brassica napus*. Again, these proteins are believed to be cryoprotective proteins rather than AFPs. Neven in Plant Molecular Biology 21: 291–305, 1993 describes the DNA characterisation of a spinach cryoprotective protein. Salzman in Abstracts and Reviews of the 18th Annual Meeting of the ASEV/Eastern Section in Am. J. Enol. Vitic., Vol. 44, No. 4, 1993 describes the presence of boiling-stable polypeptides in buds of Vitis. Although the proteins are analogous to fish antifreeze peptides, they are cryoprotective proteins and not AFPs. Lin in Biochemical and Biophysical Research Communication, Vol. 183, No. 3, 1992, pages 1103–1108 and in Lin, Plant Physiology (1992) 99, 519–525 describes the 15 kDa cryoprotective polypeptide from *Arabidopsis Hakaira*. Houde in The Plant Journal (1995) 8(4), 583–593 mentions cryoprotective proteins from wheat.

Up till now, however the use of AFPs has not been applied to commercially available food products. One reason for this are the high costs and complicated process for obtaining AFPs. Another reason is that the. AFPs which until now have been suggested for use in frozen food products cannot be incorporated in the standard formulation mix, because they tend to destabilise during processing especially during the pasteurisation step. This destabilisation is believed to be caused by the denaturation of the AFPs; this is a well-known effect commonly observed for peptides and proteins.

In our non pre-published patent application: PCT/EP97/ 03634 it has been described that AFPs can be isolated from natural sources such as cold-acclimatised grass by means of a new relatively simple process. This process leads for the first time to the identification of AFPs which can conveniently be incorporated in a mix for the preparation of frozen products before the pasteurisation thereof.

This process for the recovery of AFPs from grass involves the steps of
  a) isolating a AFP containing juice from the grass;
  b) heat treating the grass or the AFP containing juice to a temperature of at least 60° C.;
  c) removing the insoluble fraction.

Step c of the above process will usually take place after steps a and b. Step a and b can be done in any desired order, for example step a followed by step b (in that case the AFP rich juice will be heated) or step b followed by step a (in that case the natural source will be heated) or step a and b simultaneously.

This process has a number of advantages. Firstly by using the process it is no longer necessary to avoid rupturing of the grass such as required in the processes according to WO 92/22581. This immediately significantly increases the commercial applicability of the process, for example as compared to WO 92/22581, because high investment costs for specific processing are no longer necessary. Also by using the high temperatures it seems possible to extract from a large group of peptides present in the grass a very active AFP which is very active with respect to ice-recrystabisaffon inhibiton properties. Thirdly, contrary to expectations, the use of high temperatures does not denature all the proteinaceous material, but does only seem to denature some of the proteins, while the remaining grass AFP have an increased temperature stability. This renders it possible to include the isolated AFPs in compositions which need to be subjected to higher temperatures e.g. a pasteurisation step. This is especially surprising, because for example the AFPs from WO 92/22581 appear not stable under heating conditions.

The process as described above includes in step b the heating of the grass or the AFP rich juice to a temperature of more than 60° C. Preferably the temperature is from 60 to 110° C., most preferably from 80 to 105° C. The heating step can take place after the isolation of the protein rich juice (step a) or before the isolation of the protein rich juice. Any suitable way to heat the juice can be used, for example conventional or microwave heating, heating optionally with an added extraction medium, steaming etc.

If an extraction medium is used, preferably it is used in small volumes to avoid unnecessary dilution of the AFP fraction. Any suitable extraction medium can be used, although the use of water is especially preferred. If desired, additives may be added to the water prior to using it as an extraction medium. Most preferred, however water substantially free of additives is used.

Applicants have also found that by the above process a very active AFP derived from grass can be derived. For the purpose of the invention the term grass encompasses members of the Gramineae family including for example perennial grass such as *Lolium perenne, Parapholis strigosa, Nardus stricta, Catapodium loliaceum* and *Lolium multiflorum, Poa trivialis, Poa pratensis* and cereal crops such as winter rye, winter wheat and winter barley. Applicants have determined the amino acid sequence of this AFP.

Surprisingly it has been found that very active AFPs which can be derived from plants are characterised by a high level of the amino acids: Serine (S), Threonine (T) and Asparagine (N). In particular applicants have found that preferred AFPs of the invention are characterised in that at least 40% of the amino acids in the protein are selected from S, T and N. Preferably the AFPs are derived from grasses, especially the Gramineae family.

The preferred molecular weight of AFPs of the invention is from 8 to 16 kDa, more preferred 10–14 kDa, where this molecular weight is determined from the gene sequence or by mass spectrometry of the unmodified form e.g. in unglycosylated form.

A second aspect of the invention relates to an AFP which can be derived from grass, said AFP having an amino acid sequence (Seq. ID No. 1) from the N-terminus of:
D-E-Q-P-N-T-I-S-G-S-N-N-T-V-R-S-G-S-K-N-V-L-A-G-N-D-N-T-V-I-S-G-D-N-N-S-V-S-G-S-N-N-T-V-V-S-G-N-D-N-T-V-T-G-S-N-H-V-V-S-G-T-N-H-I-V-T-D-N-N-N-N-V-S-G-N-D-N-N-V-S-G-S-F-H-T-V-S-G-G-H-N-T-V-S-G-S-N-N-T-V-S-G-S-N-H-V-V-S-G-S-N-K-V-V-T-D-A Also embraced in the scope of our invention are proteins having a sequence which has a high degree of similarity with the above sequence. For the purpose of the invention all RI active proteins having an amino acid sequence of at least 80% overlap with the above sequence are also embraced in the scope of the invention. More preferred is an overlap of at least 90%, most preferred more than 95%, e.g. those amino acid sequences which differ none or only one or two amino acids with the above sequence. Also isoforms of the above protein are embraced within the invention.

Also embraced within the scope of the present invention are modified versions of the above described proteins whereby said modification does not materially affect the ice recrystallisation inhibition properties, such as glycosylated versions thereof.

The AFP rich juice can be separated from the grass by any convenient process for example pressing, filtering, homogenising, extraction etc. Preferably the grass is made into small pieces or into a slurry before the protein rich fraction is collected, for example by filtering. This maceration can be done by any suitable method, for example in a blender. It will be well within the ability of the skilled person to divide the material into such a form that collection of the protein rich juice can readily take place.

After collecting and heating (in the desired order) the protein fraction the resulting AFP containing sample can then be treated by any convenient process in order to remove the insoluble fraction and retain the AFP rich liquid fraction. The insoluble fraction can be removed e.g. by filtering, precipitation etc. The AFP rich liquid can then advantageously be further processed to concentrate or isolate the AFPs to bring them in a form suitable for further use. Examples of suitable processes are drying to obtain a powder or paste, further concentration to obtain an AFP concentrate, chromatography to separate the AFPs from the extraction medium etc. Again it will be well within the ability of the skilled person to determine the suitable means and conditions for appropriate isolation.

Applicants have also determined the nucleic acid sequence that encodes the above described AFP. Accordingly a second aspect of the invention relates to a nucleic add sequence capable of encoding for the AFPs of the invention. Preferably said nucleic add has the sequence (Seq. ID No. 2) of:

Also embraced within the scope of the present invention are alleles or other nucleic acid sequences which are capable to encode the above described AFPs, for example those nucleic acid sequences wherein wrt the above sequence one or more codons have been replaced by their synonyms (i.e. codons encoding for the same amino acid).

Vectors containing a nucleic acid sequence capable of encoding the AFP of the invention are also embraced within the scope of the invention.

Based on the above information it is also possible to genetically modify other natural sources such that they produce the advantageous AFP as identified here-above.

Applicants also have found that AFPs of the above sequence have improved ice-recrystallisation inhibition properties. A suitable test for determining the ice recrystallisation inhibition properties is described in the examples and involves the quick freezing to −40° C. follow by storage for one hour at 60° C. Preferably AFPs which are subject to this test after heat-treatment result in an ice crystal particle size which is less than 5 $\mu$m larger than the ice crystal size of a sample with the same AFP which was not heat-treated. Preferably the difference is less than 3 $\mu$m, most preferred less than 1 $\mu$m.

Preferably those AFPs are chosen which have significant ice-recrystallisation inhibition properties. A suitable test for determining the recrystallisation inhibition properties is indicated in the examples. Preferably AFPs in accordance to the invention provide a ice particle size following an ice recrystallisation inhibition assay as described in the examples of 15 $\mu$m or less, more preferred from 5 to 15 $\mu$m.

The AFP of the invention can conveniently be used in food products, preferably in food products which are frozen or intended to be frozen. Especially preferred is the use of AFPs in products which are heated e.g. by pasteurisation, blanching or sterilisation prior to freezing. Especially preferred is the use in frozen confectionery products.

Examples of such food products are: frozen confectionery mixes such as ice-cream mixes and water-ice mixes which are intended to be pasteurised prior to freezing. Such mixes are usually stored at ambient temperature. Suitable product forms are for example: a powder mix which is packed for example in a bag or in sachets. Said mix being capable of forming the basis of the frozen food product e.g. after addition of water and optionally other ingredients and -optional-aeration.

Another example of a suitable mix could be a liquid mix (optionally aerated) which, if necessary after addition of further components and optional further aeration can be frozen.

The clear advantage of the above mentioned mixes is that the presence of the AFP ingredient makes that the mixes can be frozen under quiescent conditions, for example in a shop or home freezer without the formation of unacceptable ice

```
GAT GAA CAG CCG AAT ACG ATT TCT GGG AGC AAC AAT ACT GTC AGA

TCC GGG AGC AAA AAT GTT CTT GCT GGG AAT GAC AAC ACC GTC ATA

TCT GGG GAC AAC AAT AGT GTG TCT GGG AGC AAC AAC ACT GTC GTA

AGT GGG AAT GAC AAT ACC GTA ACC GGC AGC AAC CAT GTC GTA TCA

GGG ACA AAC CAT ATC GTT ACA GAC AAC AAC AAT AAC GTA TCC GGG

AAC GAT AAT AAT GTA TCC GGG AGC TTT CAT ACC GTA TCC GGG GGG

CAC AAT ACT GTG TCC GGG AGC AAC AAT ACC GTA TCT GGG AGC AAC

CAC GTT GTA TCT GGA AGC AAC AAA GTC GTG ACA GAC GCT TAA
``` crystal shapes and hence with a texture different to products normally obtained via quiescent freezing.

Very conveniently these mixes are packed in closed containers (e.g. cartons, bags, boxes, plastic containers etc). For single portions the pack size will generally be from 10 to 1000 g. For multiple portions pack sizes of up to 500 kg may be suitable. Generally the pack size will be from 10 g to 5000 g.

As indicated above the preferred products wherein the AFPs are used are frozen confectionery product such as ice-cream or water-ice. Preferably the level of AFPs is from 0.00001 to 0.5 wt % based on the final product. If dry-mixes or concentrates are used, the concentration may be higher in order to ensure that the level in the final frozen product is within the above ranges.

For the purpose of the invention the term frozen confectionery product includes milk containing frozen confections such as ice-cream, frozen yoghurt, sherbet, sorbet, ice milk and frozen custard, water-ices, granitas and frozen fruit purees. For some applications the use in fermented food products is less preferred.

Preferably a the level of solids in the frozen confection (e.g. sugar, fat, flavouring etc) is more than 4 wt %, for example more than 30 wt %, more preferred from 40 to 70wt %.

Frozen confectionery products according to the invention can be produced by any method suitable for the production of frozen confectionery. Especially preferably however all the ingredients of the formulation are fully mixed before pasteurisation and before the freezing process starts. The freezing process may advantageously involve a hardening step, for example to a temperature of −30 Celsius or lower.

EXAMPLE I

Isolation of AFPs by first heating grass, followed by isolating the AFP rich juice and isolation of the AFP. Mixed grass tissue (*Poa Trivialis, Lolium Perenne, Holcus Lanatus, Bromus Sterilis*) was cut in January (mean temperature in that month was 3.5° C. ensuring the appropriate cold acclimatization of the plants). The grass tissue was rapidly transported into the laboratory for further handling and washed thoroughly with water to remove dirt.

500 9 of grass clippings was placed in a 650 Watt microwave oven and heated at full power for 5 minutes, whereby the temperature was raised to 85 to 100° C. The grass clippings were then cooled to ambient temperature.

Alternatively the grass clippings are mixed with 500 g boiling water and the mixture is re-heated to 100° C. followed by boiling for 10 minutes under stirring and then allowed to cool to 60° C.

After the heating step the AFP rich juice was separated from the clippings by filtering. The mass was stirred continuously for 5 minutes in the presence of an equal volume of water and then squeezed through 3 layers of muslin.

The supernatant can be freeze dried to remove the water followed by storage. Alternatively the supernatant can be frozen for storage.

EXAMPLE II

A liquid premix for the preparation of ice-cream was prepared by mixing:

| Ingredient | % by weight |
| --- | --- |
| Skimmed milk powder | 10.00 |
| sucrose | 13.00 |

-continued

| Ingredient | % by weight |
| --- | --- |
| maltodextrine (MD40) | 4.00 |
| Locust bean gum | 0.14 |
| butter oil | 8.00 |
| monoglyceride (palmitate) | 0.30 |
| vanillin | 0.01 |
| AFP (of example I*) | 0.01 or none (control) |
| water | balance |

*Note: AFP is added as concentrated AFP solution in some of the water, percentage refers to amount of AFP.

The ingredients were mixed at ambient temperature followed by pasteurisation for 60 seconds at 89° C. The mix was aseptically filled into packs of 500 ml, sealed and stored at ambient temperatures.

The mix can be used for the preparation of ice-cream by whipping it with a conventional house-hold mixer to an overrun of about 70% followed by freezing under quiescent conditions in a house-hold freezer.

After two months storage the composition according to the invention had a markedly better texture than the control sample.

EXAMPLE III

The ice recrystallisation inhibition properties of the AFPs can determined as follows:

A sample of an AFP containing product was adjusted to a sucrose level of 30 wt % (If the starting level of the sample was more than 30% this was done by dilution, if the starting level was lower sucrose was added to the 30% level).

A 3 $\mu L$ drop of the sample was placed on a 22 mm coverslip. A 16 mm diameter cover-slip was then placed on top and a 200 g weight was placed on the sample to ensure a uniform slide thickness. The edges of the coverslip were sealed with clear nail varnish.

The slide was placed on a Linkham THM 600 temperature controlled microscope stage. The stage was cooled rapidly (50° C. per minute) to −40° C. to produce a large population of small crystals. The stage temperature was then raised rapidly (50° C. per minute) to −6° C. and held at this temperature. 25 The ice-phase was observed at −6° C. using a Leica Aristoplan microscope. Polarised light conditions in conjunction with a lambda plate were used to enhance the contrast of the ice crystals. The state of the ice phase (size of ice crystals) was recorded by 35 mm photomicrography at T=0 and T=1 hour.

Generally this test can be applied to any suitable composition comprising AFP and water. Generally the level of AFP in such a test composition is not very critical and can for example be from 0.0001 to 0.5 wt %, more preferred 0.0005 to 0.1 wt %, most preferred 0.001 to 0.05 wt %, for example 0.01 wt %.

Any suitable composition comprising AFP and water can be used to carry out the test. Generally, however, it will not be necessary to obtain the AFP in purified form. For practical applications normally it would suffice to prepare a liquid extract or juice of natural material, wherein this extract or juice can then be tested.

This method can be applied for example to the AFP containing extracts as obtained in example I, with or without a concentration step.

The recrystallisation inhibition properties of several samples was measured. The AFP juices obtained after extraction and heating in accordance to example I were measured for their recrystallisation properties as above.

Non heat treated grass extract from grass harvested in January was obtained from Silsoe (UK). The extract was centrifuged for 1 hour to remove soil and insoluble debris as follows, Centrifuge: Sorvall RC3C, Rotor: H6000A, Temperature: +5° C., Rotor Speed: 5000rpm (7268g).

A sample of the extract was freeze dried to determine its total solids content. This was found to be 11.48 mg/ml. The dried extract was then rehydrated with 30% Sucrose solution to its original total solids concentration. Several solutions were prepared by diluting the extract as necessary with 30% Sucrose solution.

Ice crystal recrystallisation inhibition activity was measured using the assay as described above.

The T=0 and T=1 hour pictures from the recrystallisation inhibition assays had their mean ice crystal sizes measured using the Zeiss TGA 10 analyser. The ice-crystal size (length) was determined by drawing around the perimeter of the crystals. The maximum length for each individual ice crystal of a batch of ice cream was imported into a spreadsheet where analysis of the data set was carried out to find the mean, and standard deviation.

The results obtained are shown in the table below.

| Sample | Total Solids (mg/ml) | Ice Crystal Size ($\mu$m) | | Ice Crystal Growth in 1 hour at −6° C. ($\mu$m) |
|---|---|---|---|---|
| | | T = 0 | T = 1 hour at −6° C. | |
| Undiluted | 11.48 | 5.2 | 7.3 | 2.1 |
| 50% Extract | 5.74 | 5.5 | 7.6 | 2.1 |
| 25% Extract | 2.87 | 6.3 | 8.9 | 2.6 |
| 12.5% Extract | 1.435 | 6.6 | 13.1 | 6.5 |
| 6.25% Extract | 0.7175 | 8.1 | 14.7 | 6.6 |
| 3.125% Extract | 0.359 | 7.4 | 17.0 | 9.6 |
| 1.5625% Extract | 0.179 | 9.0 | 20.3 | 11.3 |

These results show the variation in final crystal size and the change in ice crystal size over 1 hour at −6° C. for the various dilutions of grass extract. It can be seen that the solids level in the grass extract can be varied in a wide range while still good recrystallisation inhibition properties are obtained. Preferably those concentrations are chosen which result in an ice crystal size after 1 hour of 15 micrometer or less.

A similar test was done with grass extract which had been subjected to heat treatment (10 minutes at 100° C.). No significant deterioration of recrystallisation inhibition properties was seen.

Additionally the grass extracts of example I were tested using the same recrystallisation inhibition test. The following results were obtained:

| Heat treatment | Crystal Size in $\mu$m | |
|---|---|---|
| | T = 0 | T = 1 |
| 60° C. 1 hour | 9.6 | 11.1 |
| Boil 10 minutes | 9.8 | 11.3 |

These results show that even after heating the extract of cold acclimatised grass maintained the ability to inhibit ice crystal growth.

EXAMPLE IV

Seed of perennial rye grass (*Lolium perenne*) was supplied by Barenbrug (UK) Ltd. The seed was planted in 9 inch pots in Levingtons No.2 compost and after germination, which usually occurred between 4–7 days after planting, the plants were grown on in the glass house for a further 7–10 days until they were approximately 15–20 cm high. The plants were then transferred to a cold room for cold acclimation. Acclimation was for 30 days at +4° C. with 8–16 hours light/dark.

Cold acclimated leaves were cut and homogenised in 50 mM Tris, 10 mM EDTA adjusted to the required pH with concentrated HCl. Homogenisation was for 2×30 s in a Waring blender with a 2.5:1 ratio (w/w) of buffer to leaf.

The homogenate was then placed in a boiling water bath for minutes and collected through four layers of muslin. The collected supernatant was further centrifuged at 15,000×g in the 8×50 ml rotor of a Sorvall centrifuge.

Ice recrystallisation properties were tested by the method described in example III.

Heat stable extract (10–50 ml) was concentrated approximately ten-fold in an Amicon concentrator using a PM10 membrane. 1 ml aliquots of concentrate were desalted on a Fast Desalting Column on a fast performance liquid chromatography (FPLC) separation system (Pharmacia). The column was run at 1 ml min$^{-1}$ in 50 mM Tris/Cl, 10 mM EDTA, pH8.5. Fraction (1 ml) collection was initiated as soon as the monitored O.D. 280 nm started to rise. The RI active fractions were pooled, typically in a volume of 3 ml The RI activity was loaded onto a Mono Q (HR5×5) column equilibrated in the same Tris, pH8.5 buffer. The pass was collected as a single fraction and the column was immediately eluted with a linear gradient of 0–0.25M NaCl over 25 minutes at 1 ml min$^{-1}$. The whole activity was routinely found to remain unbound eluting solely in the pass fraction.

The pass fraction was readjusted, carefully to pH9.5 using 1 microliter drops of 4M NaOH and loaded onto the Mono Q column which had been re-equilibrated in Tris buffer pH9.5. The pass was collected as a single fraction and then the column was immediately eluted with a 0–0.25M NaCl linear gradient over 25 minutes. The flow rate was 1 ml min$^{-1}$ and 1 ml fractions were collected for RI assay. The whole activity was found to have bound to the column and no activity was found in the pass fraction. Activity eluted as a single peak between 0.08 and 0.14M NaCl.

The active peak fractions from the Mono Q column were pooled, concentrated to 50 microliter on a PM10 Centricon concentrator and loaded onto a Sephadex 75 column on the Smart system (Pharmacia). The column was equilibrated in 50 mM Tris/Cl pH9.5 buffer and the flow rate was 50 microliter min$^{-1}$. Sample collection was delayed for 1.0 microliter to allow for the void volume of the column and then 50 ml fractions were collected. The active fractions were run on sodium dodecylsulphate Polyacrylamide gel electrophoresis.

Samples were run on 10% Nu Page gels from Novex. The samples and gel buffer were prepared as described in the manufacturers instructions and gels were stained using a Novex silver staining kit. The active fractions contained a single stained protein band with an apparent molecular weight of 29 kDa.

Protein samples were also separated by SDS PAGE followed by electroblotting onto polyvinylidenefluoride (PVDF) membrane based on the method of Matsudaira in 10 mM 3-(Cyclohexylamino)-1-propansulfonsyre (CAPS) buffer, pH 11.0, 10% methanol. The membrane was wetted in methanol and then equilibrated in Caps buffer for 10 minutes. Blotting was for 16 hours at 20 volts constant voltage. After blotting the proteins were visualised by staining the membrane with 0.2% coomassie brilliant blue in 50% methanol, 1% acetic acid for 1 minute. The membrane was then destained with 50% methanol until the proteins bands were clearly visible. The membrane was washed in Milli Q water, air dried and stored at −20° C.

The N-terminus of the 29 kDa band was sequenced as follows by conventional methods providing the amino acid sequence of:

The 29 kDa protein, believed to be the boiling tolerant RI active was immobilised onto PVDF membrane after separation by SDS PAGE and subjected to protein sequencing of the amino-terminus and 15 of the first 17 residues were successfully sequenced. A 27 kDa protein isolated form *Poa pratensis* was also sequenced at the N-terminus (Table 1) and shown to have a similar sequence suggesting that it is part of the same protein family. This implies that there is a single class of AFPs responsible for the boiling tolerant RI activity in Gramineae.

TABLE 1

Alignment of the N-terminal sequences of the 29 kDa boiling tolerant RI active protein from *Lolium perenne* (Seq. ID No. 3) and the 27 kDa protein from *Poa pratensis* (Seq. ID No. 4)

| Lolium | D E Q P N T I S G X N N T V R X G |
| Poa | A E T P N T I S G T N N | tolerant RI active protein from *Lolium perenne* (Seq. ID No. 3.) and the 27 kDa protein from *Poa partanis* (Seq. ID No. 4)

Lolium-DEQPNTISGXNNTVRXG poe-AETPNTISGNTT

EXAMPLE V

The initial extraction was with a 1:1 mix of phenol and chloroform followed by an extraction with chloroform. The phenol will denature the proteins exposing the hydrophobic amino acid residues allowing the protein to partition preferentially into the organic phase. The more hydrophilic nucleic acids and carbohydrates partition into the aqueous phase. Proteins with a significant degree of glycosylation may also partition into the interface. The chlorofom is present as the protein partitions more efficiently when two different organic solvents are used and the final chloroform extraction removes any remaining traces of phenol.

The heat stable extract prepared from leaves of *Lolium perenne* plants was concentrated approximately ten fold using an Amicon ultrafiltration chamber with a 10 kDalton cut-off membrane. The resulting concentrate (0.05 ml) was loaded onto a Superdex 75 PC 3.2/30 gel filtration column running on a Smart microseparation system (Pharmacia). The column was eluted with 50 mM Tris/Cl buffer pH 9.5 at a flow rate of 0.05 ml min$^{-1}$ and 0.05 ml fractions collected. The fractions were assayed for ice recrystallisation inhibition activity and the most active fractions were pooled together. These were then loaded onto a Mono Q PC 1.6/5 column, equilibrated in 50 mM Tris/Cl buffer pH9.5, also run on the Smart system at a flow rate of 0.1 ml min$^{-1}$. After loading and wahing, the column was eluted with a linear gradient of 0–0.4M sodium chloride and 0.1 ml fractions collected. The fractions were assayed and the activity eluted as a single peak at approximately 0.1M sodium cloride.

The active fraction was vortexed in an equal volume of phenol:chloroform:isoamyl alcohol (1:1) for 1 minute. It was then centrifuged at 13,000×g for 30 minutes. The aqueous (upper) and organic (lower) phases were collected separately, no interface was observable. The two phases were then precipitated by the addition of ten volumes of cold acetone and held at −20° C. for 16 hours. The resulting pellets were resuspended in 50 mM tris/Cl buffer, assayed for RI activity and run on SDS PAGE.

Assay of the resuspended fractions showed that the RI activity was found to partition completely into the aqueous phase. The organic phase contained no RI activity even after the fraction had been denatured/renatured in 6M guanidine hydrochloride. This was an unexpected result as a protein would usually have been expected to partition into the organic phase, or a glycoprotein into the interface. However, analysis by SDS PAGE showed that although the majority of the proteins were in the organic phase a single protein band with an apparent molecular weight of 29 kDa was visible in the active aqueous fraction but absent from the organic phase. The band stained with a different colour from the other proteins and was very diffuse.

A similar phenol:chloroform extraction was carried out on the boiling tolerant extract prepared from the cold acclimated leaves of a broad leaved perennial meadow grass (*Poa pratensis* var Barcelona) and this also demonstrated preferential partitioning of the RI activity into the aqueous phase and a protein of apparently 27 kDa on SDS PAGE.

Protein sequencing of the N-termini of the proteins confirmed that they were identical to the AFPs described in example IV.

EXAMPLE IV.

A degenerate oligonucleotide primer (Lol 1) was designed and synthesised from the protein N-terminus sequence (ASP-GW-GLN-PRO-ASN-THR-ILE) of Seq. ID No. 4, as GAYGARCARCCAIYACIAT where Y=C+T, R=A+G and I=Inosine. (Seq. ID No. 5).

First strand cDNA was prepared from 5 μg of 30 day cold acclimated *Lolium perenne* leaf RNA using Superscript Reverse Transcriptase (Stratgene) and an oligonucleotide primer OG1 (GAGAGAGGATCCTCGAG(T) 15) (Seq. ID No. 6) according to the manufacturers instructions. 1% of the first strand cDNA was used as a template, together with Lol1 and OG1 primers, in PCR reactions. The reactions were carried out in a thermal cycler using Taq DNA Polymerase (Gibco BRL) for 30 cycles (minute at 94° C., 1 minute at 55° C. and 1 minute at 72° C.) after an initial denaturation step of 2 minutes at 94° C.

A PCR product of ~600 bp was amplified and subsequently purified from a 1% agarose gel and cloned into the pTAg vector (R&D systems) according to the manufacturers instructions. The cloned PCR product was sequenced on a Perkin Elmer (Applied Biosystems) automated DNA sequencer using T3 and T7 primers. It contained an open reading frame substantially similar to Seq. ID No. 2:

```
GAT GAA CAG CCG AAT ACG ATT TCT GGG AGC AAC AAT ACT GTC AGA

TCC GGG AGC AAA AAT GTT CTT GCT GGG AAT GAC AAC ACC GTC ATA

TCT GGG GAC AAC AAT AGT GTG TCT GGG AGC AAC AAC ACT GTC GTA

AGT GGG AAT GAC AAT ACC GTA ACC GGC AGC AAC CAT GTC GTA TCA
```

```
                        -continued
GGG ACA AAC CAT ATC GTT ACA GAC AAC AAC AAT AAC GTA TCC GGG

AAC GAT AAT AAT GTA TCC GGG AGC TTT CAT ACC GTA TCC GGG GGG

CAC AAT ACT GTG TCC GGG AGC AAC AAT ACC GTA TCT GGG AGC AAC

CAC GTT GTA TCT GGA AGC AAC AAA GTC GTG ACA GAC GCT TAA
``` and the deduced amino acid sequence was substantially similar to Seq. ID No. 1:
D-E-Q-P-N-T-I-S-G-S-N-N-T-V-R-S-G-S-K-N-V-L-A-G-N-D-N-T-V-I-S-G-D-N-N-S-V-S-G-S-N-N-T-V-V-S-G-N-D-N-T-V-T-G-S-N-H-V-V-S-G-T-N-H-I-V-T-D-N-N-N-N-V-S-G-N-D-N-N-V-S-G-S-F-H-T-V-S-G-G-H-N-T-V-S-G-S-N-N-T-v-s-G-S-N-H-V-v-S-G-S-N-K-V-V-T-D-A The open reading frame codes for a protein of ~12 kDa molecular weight, which is considerably less than the apparent molecular weight on SDS PAGE of 29 kDA. The coding sequence is also observed to contain six recognised glycosylation sites (ASN-X-SER/THR) and a substantial number of SER and THR residues which may also be glycosylated. This evidence suggests that the native protein isolated from Lolium is highly glycosylated. However protein that has been enzymically deglycosylated still retains ice recrystallisation inhibition activity suggesting that the glycosylation is not essential for the protein to be active. EXAMPLE VII To prove that the *Lolium perenne* cDNA described in example VI codes for an AFP, expression of the coding region was carried out. A strain of *Pichia pastoris*, a methylotrophic yeast, was created containing the Lolium AFP cDNA.

The Lolium cDNA was cloned into a pPIC9 vector with an α—factor signal sequence to ensure secretion from the cell and glycosylation. All enzymes were from Boehringer Mannheim and used according to the manufacturers instructions. Construction of expression vectors, transformation and growth of Pichia were all as described in the invitrogen Pichia Expression Kit (Version B) Manual.

The Lolium cDNA was cloned into the pPIC9 vector as a PCR amplification fragment, with compatible restriction ends for ligation into the pPIC9 vector. This was produced using Lolium cDNA as the template and the primers GTATCTCTCGAGAAAAGAGATGAGCAGC-CGAACACGATT (SEQ. ID No. 7) and TTAATTCGCG-GCCGCCTGTAGGAAAAGTATGGTATATC (SEQ. ID. No. 8) which introduced a XhoI restriction site at the 5 end and a NotI restriction site at the 3' end of the amplification fragment and ensured that the Lolium cDNA was in frame with the secretion signal open reading frame. The reactions were carried out in a thermal cycler using Taq DNA polymerase and Pfu proof reading enzyme (Boehringer Mannheim) for 30 cycles (1 minute at 94° C. 1 minute at 55° C. and 1 minute at 72° C.). All subsequent PCR reactions were carried out under the same conditions but without Pfu enzyme. The XhoI/NotI cDNA fragment was then cloned into the XhoI/NotI digested pPIC 9 vector and transformed into competent *E. Coli* cells (strain XL1-blue). After transformation, they were plated onto LB plates with 50 μg ml ampicillin and grown at 37° C. for 16 hours. Then, 20 ampicillin resistant transformants were picked and analysed for integration of the Lolium cDNA by PCR using the 5' AOX1 and the 3' AOX1 primers that had been synthesised as specified in the invitrogen Kit Manual.

Plasmid DNA was isolated from four positive transformants by miniprep and linearised by digestion with SalI for transformation into Pichia cells that had been grown and washed as described in the invitrogen Manual. The linearised DNA digests were electroporated into the Pichia cells using a BioRad GeneFulser as recommended and after addition of ice cold 1M sorbitol spread on MD plates and grown at 30° C. for 24 hours until colonies were visible. 16 transformants were then picked onto fresh MM and MD plates and transformants that grew normally on the MD plates but more slowly on the MM plates were selected. These transformants were then analysed by PCR using the 5' and 3' AOX1 primers and 8 positives were tested for expression.

Initially the colonies were inoculated into BMGY medium and grown at 30° C. for 24 hours after which the cells were spun down and transferred to BMMY medium to induce expression and returned to 30° C. for a further 24 hours. Two more additions of methanol to 0.5% were made at 24 and 48 hours to maintain induction. The cells were then removed by centrifugation and an aliquot of the medium adjusted to 30% sucrose and assayed for ice recrystallisation inhibition activity. The medium of all the transformants contained significant RI activity whereas medium produced in the same way from control Pichia without the integrated Lolium cDNA had no activity.

The above example demonstrates that the protein isolated from *Lolium perenne* and the corresponding cDNA represent an RI active AFP.

EXAMPLE VIII

*E. coli* XL-1 blue was used for all cloning steps; cultures were grown on 2YT medium with selection by Ampicillin or Kanamycin as appropriate. All oligonucleotide primers were synthesized on a Perkin Elmer 381 A DNA Synthesiser, using the phosphoramidite method as recommended by the manufacturers. Nurse culture plates were prepared by plating 2 ml of a cell suspension of *Nicotiana bethiama* on a petri dish containing 25 ml of MS salts. B5 vitamins (1 mg L nicotinic acid, 1 mg L pyridoxine, 10 mg L thiamine, 100 mg L inisitol)+1 mg L 2–4 D, 0.2 mg L BAP & 0.8% agar. The cells were swirled to cover the agar and then covered with a sterile filter paper disc.

Selection media=MS basal media+3% sucrose, 0.2 mg L IAA, 1 mg L BAP, 0.9% agar+500 mg L cefotaxime & 100 mg L kanamycin.

The Lol1 sequence encoding the AFP, and a PR1a apoplastic targeting sequence, were PCR amplified with 5' and 3' oligonucleotide primers designed to generate the appropriate restriction sites to allow them to be ligated together at a BamHI site and the annealed product inserted into an NcoI/EcoRI opened pUC intermediate plasmid vector (Messing 1983). The Lol1 AFP was separately inserted into three pUC vectors behind different promoter sequences (Granule bound starch synthase; cauliflower etched ring virus; double 35 S cauliflower mosaic virus). They were then further cloned into a plant transformation binary vector and introduced into tobacco using Agrobacterium mediated transformation.

PCR reaction mixtures contained 5 μl of ×10 Taq reaction buffer, 1 μl of dNTPs, 1 μl of 5' and 3' primers (50 pmol μl), 1 μl of template Lol1, 0.5 μl of Taq polymerase and 0.05 μl of pfu proof reading enzyme. Tubes were overlayed with mineral oil and subjected to 30 cycles of 1 minute at 94° C., 1 minute at 55° C. and 1 minute at 72° C. after an initial denaturation step of 2 minutes at 94° C.

Digestions of PCR amplification products were carried out with the appropriate restriction enzymes in the recommended buffer (Boehringer Mannheim) for 16 hours at 37° C. Digestion mixtures were separated on a 1% agarose gel and the relevant bands excised and purified using the Qiagen quick DNA gel purification kit following the manufacturers recommendations.

Insert and plasmid vector were ligated with T4 ligase and ×10 buffer as recommended by Stratgene for 16 hours at 16C. Competent *E.coli* cells were transformed using 2 μl of ligation reaction, plated out and grown at 37° C. overnight. Transformants were identified by PCR using specific 5 and 3' primers. Plasmid DNA was then isolated as described in Maniatis Volume 1 and correct assembly confirmed by restriction digest analysis.

The HindIII/EcoRI inserts were excised and ligated as before into HindIII/EcoRI digested general plant transformation vector (GPTV). Competent *E.coli* were transformed and transformants identified by PCR; subsequently isolated plasmid DNA was confirmed to be correct by sequencing.

The three different GPTV vectors were separately transformed into *Agrobacterium tumafaciens* (strain LBA 4404) using the freeze thaw method as described in the Plant Molecular Biology manual PMAN A3\7.

*Nicotiana tabacum* (var Petit Havana) seeds were surface sterilised for 10 minutes with a solution of 10% sodium hypochlorite and after rinsing three times with distilled water, were transferred to Murashige & Skoog basal medium+3% sucrose+0.9% agar. The seeds were grown for two weeks and then thinned to 2 per vessel after which sterile plantiets were obtained by taking monthly shoot cuttings into MS basal medium+3% sucrose+0.9% agar. Agrobacterium cells containing the appropriate plasmid were cultured overnight in Lennox broth (5 g $L^{-1}$ NaCl, 10 g $L^{-1}$ yeast extract, 10 g L bacto tryptone and 15 g L agar), after which they were recovered by centrifuging for 10 minutes at 3000×g and resuspended in MS basal medium+3% sucrose. Tobacco leaf discs cut with a sterile cork borer were infected by incubating for 10 minutes with the Agrobacterium culture after which they were patted dry on sterile filter paper and plated face down on a nurse culture plate of tobacco cells.

The infected leaf discs were incubated at 26° C. for 2 days in a light intensity of 2000 lux and then removed from the nurse culture plates to selection media. They were then incubated at 3000 lux, 26° C., 16 hours day/8 hours dark and transferred every two weeks to fresh media. As new growing shoots appeared at the edge of the disc they were removed to MS basal media+3% sucrose, 500 mg L cefotaxime & 100 mg L kanamycin for rooting.

After rooting and growing to a size where they had 3–4 leaves a leaf from several lines of each construct plus several untransformed control plants was removed for RI assay. The leaf tissue was ground in a eppendorf tube and the sap released was recovered by centrifugation. The sap was adjusted to 30% sucrose (w/v) prior to assay.

Several plant lines from each construct were demonstrated to have significant levels of ice recrystallisation inhibition activity. Extracts from each of the control plants possessed no activity. This clearly demonstrated that the Lol1 AFP had been transformed into tobacco, a plant that does not have its own AFP, and was successfully expressed as an active protein with no need for cold acclimation.

Plants selected to be grown on, were potted into a 50% perlite/50% peat mix and re-potted to flowering in a 26° C. 16 hour light/22° C. 8 hour dark cycle in a growth room. Flowers were bagged to ensure self-pollination and seed collected and stored at +4° C.

EXAMPLE IX

To prove that the AFP of the invention does not require glycosylation to be active, the coding region was expressed in a prokaryote system. A strain of *Escherichia Coli* was created containing the Lolium AFP cDNA.

The Lolium cDNA was cloned into a pET32 plasmid from Novagen that contains thioredoxin for expression of the target gene as a fusion protein. All enzymes were from Boehringer Mannheim and used according to the manufacturers instructions. Construction of expression plasmids, transformation and growth of *E.Coli* were all as described in the Novagen pET system manual and Promega Applications guide.

The Lolium cDNA was cloned into the pET-32 plasmid as a PCR amplification fragment, with compatible restriction ends for ligation into the multiple cloning site of the pET-32 plasmid. This was produced using Lolium cDNA as the template and a 5' oligonucleotide primer (TTTGCGCTCGAGTTAAGCGTCTGTCACGACTTTG (Seq. ID No. 9) and 3' oligonucleotide primer (TTTGCGCCATGGATGAACAGCCGAATACGATTTC) (Seq. ID No. 10). This introduced a NcoI restriction site at the 5' end and a XhoI restriction site at the 3' end of the amplification fragment. The reactions were carried out in a thermal cycler using Taq DNA polymerase for 25 cycles (denaturation at 94° C., annealing from 35° C. to 60° C., expression at 72° C.). All subsequent PCR reactions were carried out under the same conditions. The NcoI/XhoI PCR amplified fragment was hen cloned into the NcoI/XhoI digested pET-32 plasmid and transformed into competent non-expression *E.Coli* cells (strain XL1-Blue). After transformation, they were plated onto LB-ampicillin plates and grown at 37° C. for 16 hours. 10 ampicillin resistant transformants were picked and analysed for integration of the Lolium cDNA by PCR using the pET upstream and downstream primers from Novagen.

Plasmid DNA was isolated from 3 positive transformants by miniprep and digested by XhoI and NcoI for transformation into the competent expression *E.Coli* BL21(DE3) cells as described in the pET system manual. The transformed cells were plated onto LB-Ampicillin medium and incubated at 37° C. for 24 hours together with a control made with non transformed BL21(DE3) *E.Coli* cells.

Three positive transformant colonies were selected and subcultured in LB-ampicillin media and incubated at 37° C. for 1 hour to reached an O.D.(λ=600 nm) of 0.6 and then inoculated in a larger medium volume and shaken at 37° C. When the O.D. reached 0.5, the cells were induced with IPTG for protein expression for 3 hours as described in the pET system manual.

Expressed proteins were isolated from the *E.Coli* cells cytoplasm as described in the pET system manual; cells were harvested by centrifugation, resuspended in HEPES buffer (25 mM HEPES, 10 mM $MgCl_2$, 100 mM NaCl, 1 mM DTT, pH7.5) and sonicated for 10 seconds. The cytoplasmic protein fraction was centrifuged and the supernatant collected. An aliquot of the supernatant was adjusted to 30% sucrose and assayed for ice recrystallisation inhibition activity as described in example III. The cytoplasmic protein extract demonstrated significant RI activity whereas the cytoplasmic protein extract produced in the same way from control *E.Coli* cells without the integrated Lolium cDNA had no activity.

The fusion protein was purified by metal affinity column and the thioredoxin removed by digestion with thrombin. The identity of the cleaved AFP was confirmed by protein sequencing of the N-terminus and this cleaved protein was shown to also have significant ice recrystallisation inhibition activity.

The above provides proof that the non-glycosylated *Lolium perenne* antifreeze protein expressed in *E.Coli* retained its recrystallisation inhibition activity, both as a fusion product with thioredoxin and after thrombin cleavage.

What is claimed is:

1. An isolated anti-freeze protein characterised in that said protein has at least 80% sequence identity the following amino acid sequence D-E-Q-P-N-T-I-S-G-S-N-N-T-V-R-S-G-S-K-N-V-L-A-G-N-D-N-T-V-I-S-G-D-N-N-S-V-S-G-S-N-N-T-V-V-S-G-N-D-N-T-V-T-G-S-N-H-V-V-S-G-T-N-H-I-V-T-D-N-N-N-N-V-S-G-N-I-D-N-N-V-S-G-S-F-H-T-V-S-G-G-H-N-T-V-S-G-S-N-N-T-V-S-G-S-N-H-V-V-S-G-S-N-K-V-V-T-D-A (SEQ ID NO: 1)

as well as modified versions thereof wherein the modification does not materially affect the ice recrystallisation inhibition properties.

2. The isolated anti-freeze protein according to claim 1, which is derived from plant.

3. The isolated antifreeze protein according to claim 2 which is derived from a cold-acclimatised grass.

4. Anti-freeze protein of claim 1, wherein the sequence identity is at least 95%.

5. Anti-freeze protein of claim 4, wherein the sequence identity is 100%.

6. Anti-freeze protein of claim 1, wherein the protein has been modified by glycosylation.

7. An isolated antifreeze protein which naturally is derived from a plant and characterised in that at least 40% of its amino adds are from the group of serine, threonine and asparagine.

8. The isolated antifreeze protein according to claim 7 which has been isolated from a plant.

9. The isolated antifreeze protein according to claim 8 which has been isolated from a cold-acclimatised grass.

10. The isolated antifreeze protein according to claim 7 which is produced recombinantly.

* * * * *

SEQUENCE LISTING

<160> NUMBER OF SEQ ID NOS: 10

<210> SEQ ID NO 1
<211> LENGTH: 118
<212> TYPE: PRT
<213> ORGANISM: Lolium perenne

<400> SEQUENCE: 1

Asp Glu Gln Pro Asn Thr Ile Ser Gly Ser Asn Asn Thr Val Arg Ser
1               5                   10                  15

Gly Ser Lys Asn Val Leu Ala Gly Asn Asp Asn Thr Val Ile Ser Gly
            20                  25                  30

Asp Asn Asn Ser Val Ser Gly Ser Asn Asn Thr Val Val Ser Gly Asn
        35                  40                  45

Asp Asn Thr Val Thr Gly Ser Asn His Val Val Ser Gly Thr Asn His
    50                  55                  60

Ile Val Thr Asp Asn Asn Asn Val Ser Gly Asp Asn Asn Val
65                  70                  75                  80

Ser Gly Ser Phe His Thr Val Ser Gly Gly His Asn Thr Val Ser Gly
                85                  90                  95

Ser Asn Asn Thr Val Ser Gly Ser Asn His Val Val Ser Gly Ser Asn
            100                 105                 110

Lys Val Val Thr Asp Ala
        115

<210> SEQ ID NO 2
<211> LENGTH: 357
<212> TYPE: DNA
<213> ORGANISM: Lolium perenne

<400> SEQUENCE: 2
gatgaacagc cgaatacgat ttctgggagc aacaatactg tcagatccgg gagcaaaaat      60
gttcttgctg ggaatgacaa caccgtcata tctggggaca caatagtgt gtctgggagc     120 aacaacactg tcgtaagtgg gaatgacaat accgtaaccg gcagcaacca tgtcgtatca    180
gggacaaacc atatcgttac agacaacaac aataacgtat ccgggaacga taataatgta    240
tccgggagct ttcataccgt atccgggggg cacaatactg tgtccgggag caacaatacc    300
gtatctggga gcaaccacgt tgtatctgga agcaacaaag tcgtgacaga cgcttaa       357

<210> SEQ ID NO 3
<211> LENGTH: 17
<212> TYPE: PRT
<213> ORGANISM: Lolium perenne
<220> FEATURE:
<221> NAME/KEY: UNSURE
<222> LOCATION: (10)..(10)
<223> OTHER INFORMATION: residue not identified by sequencer
<221> NAME/KEY: UNSURE
<222> LOCATION: (16)..(16)
<223> OTHER INFORMATION: residue not identified by sequencer

<400> SEQUENCE: 3

Asp Glu Gln Pro Asn Thr Ile Ser Gly Xaa Asn Asn Thr Val Arg Xaa
1               5                   10                  15

Gly

<210> SEQ ID NO 4
<211> LENGTH: 12

```
<212> TYPE: PRT
<213> ORGANISM: Poa pratensis

<400> SEQUENCE: 4

Ala Glu Thr Pro Asn Thr Ile Ser Gly Thr Asn Asn
1               5                   10

<210> SEQ ID NO 5
<211> LENGTH: 20
<212> TYPE: DNA
<213> ORGANISM: Artificial Sequence
<220> FEATURE:
<223> OTHER INFORMATION: PCR primer
<221> NAME/KEY: modified_base
<222> LOCATION: (12)..(12)
<223> OTHER INFORMATION: i
<221> NAME/KEY: modified_base
<222> LOCATION: (18)..(18)
<223> OTHER INFORMATION: i

<400> SEQUENCE: 5
gaygarcarc cnaayacnat                                              20

<210> SEQ ID NO 6
<211> LENGTH: 32
<212> TYPE: DNA
<213> ORGANISM: Artificial Sequence
<220> FEATURE:
<223> OTHER INFORMATION: PCR primer

<400> SEQUENCE: 6
gagagaggat cctcgagttt tttttttttt tt                                32

<210> SEQ ID NO 7
<211> LENGTH: 39
<212> TYPE: DNA
<213> ORGANISM: Artificial Sequence
<220> FEATURE:
<223> OTHER INFORMATION: PCR primer

<400> SEQUENCE: 7
gtatctctcg agaaaagaga tgagcagccg aacacgatt                         39

<210> SEQ ID NO 8
<211> LENGTH: 38
<212> TYPE: DNA
<213> ORGANISM: Artificial Sequence
<220> FEATURE:
<223> OTHER INFORMATION: PCR primer

<400> SEQUENCE: 8
ttaattcgcg gccgcctgta ggaaaagtat ggtatatc                          38

<210> SEQ ID NO 9
<211> LENGTH: 34
<212> TYPE: DNA
<213> ORGANISM: Artificial Sequence
<220> FEATURE:
<223> OTHER INFORMATION: PCR primer

<400> SEQUENCE: 9
tttgcgctcg agttaagcgt ctgtcacgac tttg                              34

<210> SEQ ID NO 10
<211> LENGTH: 34
<212> TYPE: DNA
<213> ORGANISM: Artificial Sequence
```

-continued

```
<220> FEATURE:
<223> OTHER INFORMATION: PCR primer

<400> SEQUENCE: 10
tttgcgccat ggatgaacag ccgaatacga tttc                                    34
```